US00PP30316P2

(12) United States Plant Patent
Tsukahara

(10) Patent No.: US PP30,316 P2
(45) Date of Patent: Mar. 26, 2019

(54) ***PETUNIA* PLANT NAMED 'SAKPET104'**

(50) Latin Name: *Petunia hybrida*
Varietal Denomination: SAKPET104

(71) Applicant: Sakata Seed Corporation, Yokohama (JP)

(72) Inventor: Jun Tsukahara, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 15/732,513

(22) Filed: Nov. 21, 2017

(51) Int. Cl.
*A01H 5/02* (2018.01)

(52) U.S. Cl.
USPC ..... Plt./356.13

(58) Field of Classification Search
USPC ..... Plt./263.1, 356.1, 356.13
See application file for complete search history.

(56) References Cited

PUBLICATIONS

Sakata 2018 & 2019 Ornamentals Catalog. http://www.gradinaspa.com/part/03-Katalog-SAKATA-2018-2019-Americko-trziste.pdf. 2 pages.*

* cited by examiner

*Primary Examiner* — Susan McCormick Ewoldt
*Assistant Examiner* — Karen M Redden
(74) *Attorney, Agent, or Firm* — Barbara Campbell; Cochran Freund & Young LLC

(57) ABSTRACT

A *Petunia* plant particularly distinguished by having pink and white bi-color star patterned flowers and a semi-trailing, semi-creeping habit, is disclosed.

1 Drawing Sheet

Genus and species: *Petunia hybrida.*
Variety denomination: 'SAKPET104'.

BACKGROUND OF THE NEW PLANT

The present invention comprises of a new and distinct cultivar of *Petunia*, botanically known as *Petunia hybrida*, and hereinafter referred to by the cultivar name 'SAKPET104.' 'SAKPET104' characterized by having pink and white star-patterned bi-colored flowers with a mounding plant habit. 'SAKPET104' originated from a hybridization in Kakegawa, Japan, in 2012. The female parent was a proprietary *Petunia* breeding line named '8BCR-23A-1D-V1' (unpatented) having pink and white striped flowers with a semi-creeping plant habit. The male parent was a proprietary *Petunia* breeding line named '8BCR-23A-1D-V2' (unpatented) having pink and white flowers with a semi-creeping plant habit.

In June 2012, '8BCR-23A-1D-V1' and '8BCR-23A-1D-V2' were crossed in Kakegawa, Japan and 100 seeds were obtained. In February 2013, the $F_1$ seed was sown in the greenhouse, cultivated and 30 plants were produced with flower colors of pink with white stripes and pink and mounding, semi-mounding and semi-creeping plant habits. In June 2013, two plant lines were selected within the $F_1$ plants that both had pink with white striped flowers and a semi-creeping plant growth habit, and crossed. Seeds from this cross were sowed in November 2013 in Salinas, Calif. and further evaluated from February 2014 through March 2014 for day-neutral flowering response. A single plant was selected and named 'L2014-PT066' and was further evaluated for day length neutral flowering response. In March 2014, 'L2014-PT066' was vegetatively propagated in Salinas, Calif., cultivated and transplanted to the field for outdoor evaluation. In January 2015, the breeder further confirmed 'L2014-PT066' to be fixed and stable. 'L2014-PT066' was subsequently named 'SAKPET104' and its unique characteristics were found to reproduce true to type in successive generations of asexual propagation.

SUMMARY

The following are the most outstanding and distinguishing characteristics of this new variety when grown under normal horticultural practices in Salinas, Calif.
1. Pink and white bi-color star patterned flowers; and
2. A semi-trailing, semi-creeping habit.

DESCRIPTION OF THE PHOTOGRAPHS

This *Petunia* plant is illustrated by the accompanying photographs which show the plant's overall plant habit including form, foliage, and flowers. The photographs are of a 3-months from transplant into 8-inch pots from rooted cuttings in Salinas, Calif. under greenhouse conditions. The colors shown are as true as can be reasonably obtained by conventional photographic procedures.

DESCRIPTION OF THE NEW VARIETY

Figure 1:
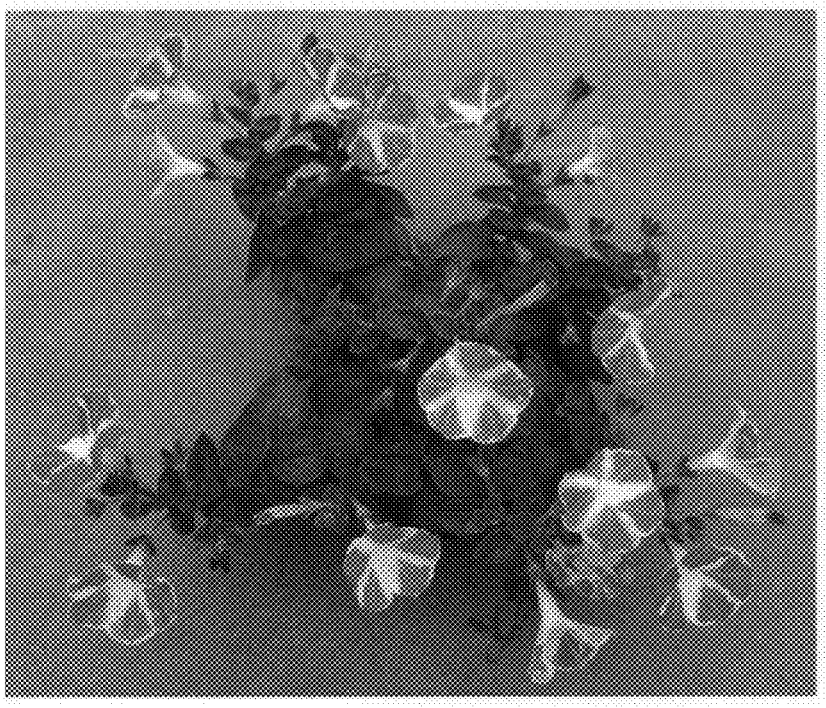
FIG. 1 shows the overall plant habit of the plant grown in a pot.
Figure 2:
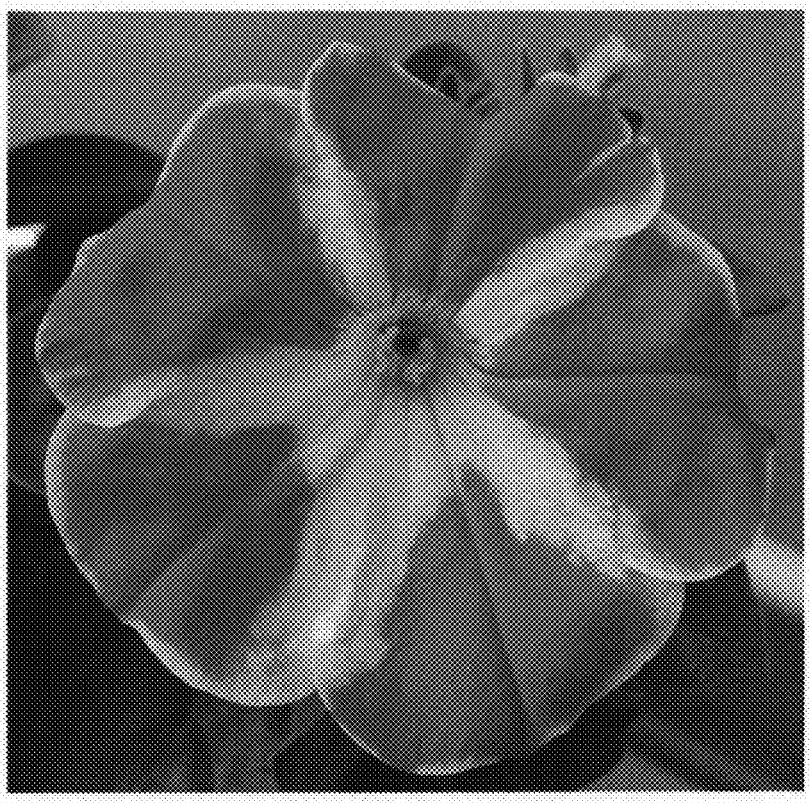
FIG. 2 shows a close-up of the mature flower of the plant.

The following traits and characteristics describe the new variety. Data obtained from plants grown 3-months from transplant into 8-inch pots from rooted cuttings in Salinas, Calif., under greenhouse conditions. Plants were pinched once during growth. Color references are to The Royal Horticultural Society of London Colour Chart (R.H.S.), 4th edition (2001). Anatomic labels are from *The Cambridge Illustrated Glossary of Botanical Terms*, by M. Hickey and C. King, Cambridge University Press.

Classification:

*Family*.—Solanaceae.

*Botanical*.—*Petunia hybrida*.

*Common*.—*Petunia*.

*Designation*.—'SAKPET104'.

Growth:

*Environmental conditions for plant growth*.—The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:

*Form*.—Semi-trailing.

*Habit*.—Semi-creeping.

*Height*.—About 24.0 cm from soil line to the top of the foliage.

*Spread*.—About 44.0 cm.

*Number of branches*.—6 main basal branches; many secondary and tertiary branches.

*Length of branches*.—16.0 cm to 24.0 cm.

*Diameter of branches*.—3.0 mm to 5.0 mm.

*Life cycle*.—Annual; tender perennial in warm climates.

*Time to produce a rooted cutting*.—About 4 weeks.

*Time to bloom from propagation*.—6 to 8 weeks.

*Flowering requirements* (*season*).—Will flower so long as temperature is above 13° C. and greater than 12 hours of daylight.

*Resistance and susceptibility*.—No particular resistance or susceptibility observed.

*Temperature tolerances*.—No particular temperature tolerances observed.

Stems:

*Stem color*.—Closest to RHS 144B (Yellow-Green) with slight RHS N92A (Violet-Blue).

*Anthocyanin color*.—RHS N92A (Violet-Blue).

*Stem pubescence*.—Heavy.

*Stem pubescence color*.—RHS N155A (White).

*Stem description*.—Pliable; circular shape in cross-section.

*Length*.—9.0 cm to 13.0 cm.

*Diameter*.—3.0 mm.

*Internode length*.—About 1.4 cm.

Leaves:

*Arrangement*.—Alternate.

*Shape*.—Ovate.

*Apex*.—Obtuse.

*Base*.—Attenuate.

*Attachment*.—Sessile.

*Margin*.—Entire.

*Surface appearance*.—Dull, waxy and sticky.

*Venation pattern*.—Pinnate.

*Venation color*.—Upper vein color: RHS 147C (Yellow-Green). Lower vein color: RHS 144D (Yellow-Green).

*Length*.—3.7 cm.

*Width*.—3.2 cm.

*Color*.—Upper surface: Closest to RHS 137A (Green. Lower surface: Closest to RHS 146B (Yellow-Green).

*Variegation*.—Absent.

*Fragrance*.—Absent.

*Surface pubescence*.—Slight.

*Surface pubescence color*.—RHS N155A (white).

*Petiole*.—Absent.

Flowers:

*Number of flowers in bloom*.—25.

*Number of flowers per node*.—1.

*Type*.—Solitary.

*Fragrance*.—Absent.

*Flower depth*.—About 5.0 cm.

*Flower diameter*.—6.5 cm.

*Peduncle*.—Length: 2.5 cm. Diameter: 2.0 mm. Color: RHS 144A (Yellow-Green) with moderate pubescence; pubescence color is RHS N155A (White).

Bud:

*Bud surface*.—Dull, sticky, heavy pubescence; pubescence color is RHS N155A (White).

*Bud length*.—4.6 cm.

*Bud diameter*.—8.0 mm.

*Bud shape*.—Cylindrical.

*Bud color*.—Closest to RHS N144D (Yellow-Green) with alternations of RHS 79D (Purple) and RHS 157D (Green-White) at the tip.

Corolla:

*Shape*.—Funnel-shaped with five fused petals.

*Diameter*.—6.5 cm.

*Depth*.—1.0 cm.

*Tube length*.—4.0 cm.

*Tube diameter*.—1.0 cm.

*Tube pubescence*.—Heavy.

*Tube pubescence color*.—RHS N155A (white).

*Color*.—Inner surface of tube: Closest to RHS 155C (White) but pure white with RHS 145B (Yellow-Green) venation. Outer surface of tube: Closest to RHS 155C (White) but pure white with RHS 145B (Yellow-Green) venation.

*Petals*.—Pubescence: Glabrous. Length: 2.8 cm. Width: 3.6 cm. Shape: Obcordate. Apex: Abruptly acute. Margin: Entire. Color: Upper surface: Closest to RHS 155C (White) but pure white in a star pattern with the points at petal fissures and at edge of petals and RHS N74B (Red-Purple) defining white star pattern and very slight RHS 145B (Yellow-Green) at the mid-vein. Lower surface: Closest to RHS 155C (White) but pure white in a star pattern with the points at petal fissures and at edge of petals and RHS 73A (Red-Purple) defining white star pattern and RHS 145B (Yellow-Green) at the mid-vein.

Sepals:

*Form.*—5, free.

*Attachment.*—Sessile.

*Apex.*—Obtuse.

*Base.*—Attenuate.

*Margin.*—Entire.

*Length.*—1.7 cm.

*Width.*—4.0 mm.

*Color.*—Upper surface: RHS 138A (Green). Lower surface: RHS 138A (Green).

Reproductive organs:

*Stamens.*—Stamen form: Arranged adjacent to pistil. Stamen number: 5, free. Stamen length: 2.1 cm to 2.5 cm. Filament color: RHS 157D (Green-White). Anther color: Closest to RHS 160B (Greyed-Yellow). Pollen color: Closest to Closest to RHS 160B (Greyed-Yellow). Pollen description: Powdery; abundant.

*Pistil.*—Pistil number: 1. Pistil length: 2.2 cm. Stigma color: RHS 144B (Yellow-Green). Stigma length: 2.0 mm. Style color: Closest to RHS 145B (Yellow-Green). Style length: 2.0 cm. Ovary arrangement: Superior.

*Seed production.*—Absent.

COMPARISON WITH PARENTAL LINES AND KNOWN VARIETY

'SAKPET104' is a new and distinct cultivar of *Petunia* owning to its pink and white star-patterned bi-colored flowers and mounding plant habit. 'SAKPET104' is most similar to the commercial *Petunia* variety COLORWORKS 'Violet Star' (U.S. Plant Pat. No. 28,564), however, there are differences as listed in the Table 1 below:

TABLE 1

Comparison with Similar Variety

| Characteristic | 'SAKPET104' | COLOR WORKS 'Violet Star' |
|---|---|---|
| Petal color, upper surface | Closest to RHS 155C (White) but pure white in a star pattern with the points at petal fissures and at edge of petals and RHS N74B (Red-Purple) defining white star pattern and very slight RHS 145B (Yellow-Green) at mid-vein | Closest to RHS N78A (Purple) and RHS N155C (White) with RHS N79A (Purple) at mid-vein |
| Petal color, lower surface | Closest to RHS 155C (White) but pure white in a star pattern with the points at petal fissures and at edge of petals and RHS 73A (Red-Purple) defining white star pattern and RHS 145B (Yellow-Green) at the mid-vein | Closest to RHS 77A (Purple) and RHS N155C (White) |
| Flower diameter | 6.5 cm | 5.8 cm |
| Plant growth habit | Semi-creeping and semi-trailing | Mounding |

When 'SAKPET104' is compared to the parental lines, the following differences can be found below in Table 2.

TABLE 2

Comparison with Parental Lines

| Characteristic | 'SAKPET104' | Female parent '8BCR-23A-1D-V1' | Male parent '8BCR-23A-1D-V2' |
|---|---|---|---|
| Flower color | Pink and white star patterned bicolor | Dark pink with white stripes | Pale pink with white stripes with a larger flower size |
| Plant growth habit | Semi-creeping | High semi-creeping habit | Low semi-creeping habit |

I claim:

1. A new and distinct variety of *Petunia* plant named 'SAKPET104' as described and illustrated herein.

* * * * *